US012765548B2

(12) United States Patent
Bodkhe et al.

(10) Patent No.: US 12,765,548 B2
(45) Date of Patent: Oct. 20, 2026

(54) ANTIMICROBIAL COMPOSITIONS AND ARTICLES MADE THEREFROM

(71) Applicant: Solventum Intellectual Properties Company, Eagan, MN (US)

(72) Inventors: Rajan B. Bodkhe, Woodbury, MN (US); Naimul Karim, Maplewood, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 774 days.

(21) Appl. No.: 18/249,572

(22) PCT Filed: Oct. 18, 2021

(86) PCT No.: PCT/IB2021/059581
§ 371 (c)(1),
(2) Date: Apr. 19, 2023

(87) PCT Pub. No.: WO2022/084831
PCT Pub. Date: Apr. 28, 2022

(65) Prior Publication Data

US 2023/0404074 A1 Dec. 21, 2023

Related U.S. Application Data

(60) Provisional application No. 63/094,964, filed on Oct. 22, 2020.

(51) Int. Cl.

| | |
|---|---|
| ***C09J 7/38*** | (2018.01) |
| ***A01N 37/36*** | (2006.01) |
| ***A61L 15/44*** | (2006.01) |
| ***A61L 15/58*** | (2006.01) |
| ***C09J 9/00*** | (2006.01) |

(52) U.S. Cl.
CPC .............. *A01N 37/36* (2013.01); *A61L 15/44* (2013.01); *A61L 15/585* (2013.01); *A61L 2300/21* (2013.01)

(58) Field of Classification Search
CPC ..... C09J 7/38; C09J 7/381; C09J 7/385; C09J 9/00
See application file for complete search history.

(56) References Cited

U.S. PATENT DOCUMENTS

| | | | | |
|---|---|---|---|---|
| 3,930,000 | A | 12/1975 | Margraf | |
| 5,614,310 | A | 3/1997 | Delgado et al. | |
| 6,497,949 | B1 | 12/2002 | Hyde et al. | |
| 6,700,032 | B1 | 3/2004 | Gray | |
| 6,998,509 | B1 | 2/2006 | Nielsen | |
| 8,137,807 | B2 | 3/2012 | Clapper et al. | |
| 2002/0034492 | A1 | 3/2002 | Munro | |
| 2002/0037977 | A1 * | 3/2002 | Feldstein | A61K 9/7053 526/60 |
| 2005/0035327 | A1 | 2/2005 | Canada et al. | |
| 2006/0210613 | A1 | 9/2006 | Carliss | |
| 2008/0081020 | A1 * | 4/2008 | Huang | A01N 31/02 424/405 |
| 2014/0018718 | A1 | 1/2014 | Rosing | |
| 2014/0234562 | A1 | 8/2014 | Traser et al. | |

FOREIGN PATENT DOCUMENTS

| | | | |
|---|---|---|---|
| CN | 1191546 | A | 8/1998 |
| CN | 101557708 | B | 1/2015 |
| CN | 102802676 | B | 2/2017 |
| CN | 106795409 | A | 5/2017 |
| CN | 104812864 | B | 7/2017 |
| EP | 0202831 | B1 | 3/1993 |
| WO | 199611572 | W | 4/1996 |
| WO | 2000007638 | A1 | 2/2000 |
| WO | 2000045864 | A1 | 8/2000 |
| WO | 02053602 | W | 7/2002 |
| WO | 2003091354 | A1 | 11/2003 |
| WO | 2005058381 | A1 | 6/2005 |
| WO | 2009108884 | A2 | 9/2009 |
| WO | 2010129199 | A2 | 11/2010 |
| WO | 2011057175 | A1 | 5/2011 |
| WO | 2012148608 | A1 | 11/2012 |
| WO | 2017040074 | A1 | 3/2017 |
| WO | 2021019336 | A1 | 2/2021 |

OTHER PUBLICATIONS

Codex Oenologique International Standards for Oenological Additives, Compiled by Chunya Zhang, China Light Industry Press. Jan. 31, 2002.
International Search Report for PCT International Application No. PCT/IB2021/059581, mailed on Jan. 28, 2022, 5 pages.

* cited by examiner

*Primary Examiner* — Michael J Feely

(57) ABSTRACT

Antimicrobial compositions and articles are disclosed, as well as method for preparing antimicrobial compositions. Also disclosed are method for using antimicrobial compositions and articles for preventing the formation or growth of biofilms, disrupting biofilms, reducing microorganism counts, and treating infections.

24 Claims, No Drawings

ANTIMICROBIAL COMPOSITIONS AND ARTICLES MADE THEREFROM

CROSS REFERENCE TO RELATED APPLICATIONS

This application is a national stage filing under 35 U.S.C. 371 of PCT/IB2021/059581, filed Oct. 18, 2021, which claims the benefit of Provisional Application No. 63/094,964, filed Oct. 22, 2020, the disclosures of each of which are incorporated by reference herein in their entireties.

BACKGROUND

Our abilities to prevent and treat microbial infections is a growing concern. More than 2% of the U.S. population suffers from non-healing (i.e., chronic) wounds, which costs the U.S. healthcare system upwards of $20 billion dollars a year to manage. Wound management often involves the use of adhesive bandages and antimicrobial compositions. Sometimes the antimicrobial compositions are used as a topical cream or ointment, while other times the antimicrobial compositions are incorporated within the adhesive itself. Either way, it is difficult to preserve the adhesive properties in the presence of the antimicrobial composition, which leads to unintended microbial exposures and frequent bandage changes.

Despite advances made in infection-control practices, surgical-site infections (SSIs) remain a substantial cause of morbidity, prolonged hospitalization, and death. In fact, SSIs are associated with a mortality rate of 3% and 75% of SSI-related deaths are directly attributable to the SSI. Surgeons rely on surgical drapes having iodine-impregnated adhesives to mitigate contact with pathogenic microbes. The antimicrobial properties, however, are typically only effective so long as the drape is securely attached to the skin.

Developing new antimicrobial adhesives with better adhesive and antimicrobial properties would help reduce rates of infections. What is needed are pressure-sensitive adhesives capable of carrying and delivering different types of antimicrobial agents.

SUMMARY

In one embodiment, an antimicrobial composition is described. The antimicrobial composition may include a polymerizable mixture comprising: at least one high Tg monomer and optionally a homopolymer thereof, wherein the homopolymer has a Tg of between about 40° C. and about 250° C.; at least one low Tg monomer and optionally a homopolymer thereof, wherein the homopolymer has a Tg of between about −70° C. and about 30° C.; an organic acid chelator, salt thereof, or combination thereof having a molecular weight less than about 400 g/mol; and a water-soluble plasticizer capable of solubilizing the organic acid chelator, or salt thereof, in an amount of at least about 100 g chelator per L of plasticizer at a temperature from about 20° C. to about 23° C. Upon polymerization, the polymerizable mixture forms a water-insoluble polymer composition comprising a copolymer derived from the at least one high Tg monomer and the at least one low Tg monomer.

In one embodiment, an antimicrobial composition is described. The antimicrobial composition may include a water-insoluble polymer composition comprising a co-polymer derived from a polymerizable mixture comprising at least one high Tg monomer and optionally a homopolymer thereof, wherein the homopolymer has a Tg of between about 40° C. and about 250° C., and at least one low Tg monomer and optionally a homopolymer thereof, wherein the homopolymer has a Tg of between about −70° C. and about 30° C.; an organic acid chelator, salt thereof, or combination thereof having a molecular weight less than about 400 g/mol; and a water-soluble plasticizer capable of solubilizing the organic acid chelator, or salt thereof, in an amount of at least about 100 g chelator per L of plasticizer at a temperature from about 20° C. to about 23° C. The antimicrobial composition may be a pressure-sensitive adhesive.

In one embodiment, an antimicrobial article is described. The antimicrobial article may include a substrate having a first surface and a second surface opposite the first surface; and an antimicrobial composition described herein disposed on the first surface.

In one embodiment, a method for preparing an antimicrobial pressure-sensitive adhesive is described. The method may include providing an antimicrobial composition described herein; and irradiating the antimicrobial composition and photoinitiator with electromagnetic radiation at a wavelength of about 280 nm to about 500 nm for a period to at least partially cure the antimicrobial composition.

In one embodiment, a method for preparing an antimicrobial pressure-sensitive adhesive is described. The method may include providing an antimicrobial composition described herein and a photoinitiator. The method may include irradiating the antimicrobial composition and the photoinitiator with electromagnetic radiation at a wavelength of about 280 to 500 nanometres at about 0.01 to about 20 milliwatts per centimeter squared ($mW/cm^2$) average light intensity, wherein the irradiating is effective to polymerize about 5 wt % to about 70 wt % of the monomers to provide a polymeric, composition. The method may include irradiating the polymeric composition with electromagnetic radiation at a wavelength of about 280 to 500 nm wavelength at an average light intensity of greater than about 20 $mW/cm^2$ to provide the antimicrobial pressure-sensitive adhesive.

In one embodiment, a method for preventing or disrupting a biofilm on a surface is described. The method may include providing an antimicrobial article described herein and contacting the antimicrobial article to the surface for a period, wherein the contacting is effective to prevent the formation or growth of a biofilm or disrupt an existing biofilm on the surface.

In one embodiment, a method for reducing a number of microorganisms on a surface is described. The method may include providing an antimicrobial article described herein and contacting the antimicrobial article to the surface for a period, wherein the contacting is effective to reduce the number of microorganisms within an area of the surface contacted by the antimicrobial article. In one embodiment, a method for reducing a number of microorganisms on a surface is described. The method may include providing an antimicrobial article described herein and contacting the antimicrobial article to the surface for a period, wherein the contacting is effective to reduce the number of microorganisms within an area of the surface contacted by the antimicrobial article.

In one embodiment, a method for treating or preventing an infection is described. The method may include providing an antimicrobial article described herein, and contacting the antimicrobial article to a surface in need of disinfecting. The contacting may be effective to reduce one or more symptoms of infection. The contacting may be effective to prevent the onset of an infection.

In one embodiment, a kit is described. The kit may include any antimicrobial composition described herein and a set of instructions directed a user to perform the steps recited in any of the methods described herein.

DETAILED DESCRIPTION

Efforts to develop alternative antimicrobial-impregnated adhesives have been met with various challenges. For example, antimicrobial agents tend to precipitate from adhesive compositions, thereby immobilizing the antimicrobial such that it is unavailable for transfer to a surface. Moreover, blending antimicrobial agents with adhesives tends to diminish the effectiveness of the antimicrobial activities. Likewise, blending antimicrobial agents with adhesives tends to decrease the adhesive strength of the adhesive, which leads to premature failure of the adhesive. This premature adhesive failure is called 'drape drift' when referring to surgical drapes. When surgical drapes move or 'drift,' the patient's exposure to microbes is increased and the patient becomes more vulnerable to infection.

Current antimicrobial adhesive technologies are limited to a few antimicrobials largely for the reasons described above. The present disclosure is directed toward antimicrobial compositions suitable for incorporation within a pressure-sensitive adhesive without sacrificing antimicrobial activity or adhesion. The antimicrobial compositions described herein employ an organic acid chelator having antimicrobial properties and a plasticizer that aids in incorporating the organic acid chelator within the pressure-sensitive adhesive. An organic acid chelator for use in antimicrobial adhesives would be exceptionally beneficial since it is far less cytotoxic than the antimicrobials presently formulated with adhesives.

As used herein, "about" means±10 percent of a given value. For example, about 10 means 9 to 11.

As used herein, "alkyl" refers to a straight or branched hydrocarbon group. "$C_{1-6}$ alkyl" denotes the number of carbon atoms within the hydrocarbon group. For example, $C_{1-6}$ means 1-6 carbons, e.g., methyl, ethyl, propyl, isopropyl, butyl, isobutyl, sec-butyl, pentyl, hexyl, and the like.

As used herein, "copolymer" refers to a chemical compound having two or more chemically-different monomers that have undergone polymerization.

As used herein, "cycloalkyl" refers to a cyclic hydrocarbon group. A cyclic hydrocarbon group is intended to include monocyclic groups; fused, bridged and spiro bicyclic groups; fused, bridged, and spiro tricyclic groups, and the like. "$C_{5-7}$ cycloalkyl" denotes the number of carbon atoms within the cyclic hydrocarbon group. For example, cyclopentyl, cyclohexyl, cycloheptyl, norbornyl, and the like.

As used herein, "essentially free" means that there is a presence of less than 0.1 wt % with respect to the weight of the composition described.

As used herein, "derived" means that a component X may be prepared from Y constituents, e.g., a water-insoluble polymer X may be prepared from monomer(s) Y.

As used herein, "glass transition temperature" or "Tg" of any homopolymer described herein is used to characterize the respective monomer, Glass transition temperatures are measured by differential scanning calorimetry (DSC).

As used herein, "halogen" or "halogenated" refers to a group having one or more halogen atom, i.e., I, Br, Cl, or F.

As used herein, "homopolymer" refers to a chemical compound having only one monomer that has undergone polymerization. The molecular weights of the homopolymers present in the compositions described herein are not intended to be limited by the glass transition temperatures of a given homopolymer molecular weight. In other words, a composition comprising a homopolymer is not limited to the exact molecular weight of the homopolymer characterized by the stated glass transition temperature.

As used herein, "hydroxyl" or "hydroxylated" refers to a group having one or more —OH group.

As used herein, "monomer" refers to a chemical compound having at least one unsaturated polymerizable functional group, e.g., an alkenyl group (i.e., —CR═CR—, wherein R is arbitrary), alkynyl group (i.e., —C≡C—), or the like. Monomers having an alkenyl or alkynyl group are referred to herein as unsaturated monomers.

As used herein, "organic chelator acid" refers to a aliphatic or aromatic compound having at least two acid groups, i.e., $—CO_2H$, $—P(O)(OH)_2$, $—S(O)_2OH$, —S(O)OH, or a salt thereof.

As used herein, "optionally substituted" describes a chemical entity or group that may or may not be substituted with one or more recited chemical moieties. For example, a "$C_{1-6}$ alkyl group optionally substituted with one or more hydroxyl" is intended to include a non-substituted $C_{1-6}$ alkyl group or a $C_{1-6}$ alkyl group substituted with one or more —OH, e.g., 2-hydroxybutyl, or the like.

As used herein, "polymerization" refers to a chemical process in which monomers undergo a chemical reaction to form polymer chains or networks. The polymerizations described herein may be step-growth or chain-growth. The polymerizations may be radical initiated, acid or base initiated, photoinitiated, or initiated with organometallic catalysts.

As used herein, "pressure-sensitive adhesive" refers to a non-reactive, self-stick adhesive that forms a bond when pressure is applied. No solvent, water, or heat is required to activate a pressure-sensitive adhesive.

When referring to "solubility," it should be understood that the solubility of a component A in a component B refers to conditions in which only component A and component B are present, e.g., no added salts, compounds, or the like. Furthermore, any solubility values provided herein are with regard to a temperature range of about 20° C. to about 23° C. at atmospheric pressure (i.e., 760 mm/Hg). As used herein, "solubilized" or "solubilizing" means freely soluble, i.e., 1-10 mass parts solvent required to completely dissolve 1 mass part of solute. Freely soluble and completely dissolved are synonymous with homogenous.

As used herein, "preventing" or "prevent" refers to delaying or halting microbial accumulation or proliferation.

As used herein, "treating" or "treatment" refers to a reducing the number of microbes present on a surface, wherein the reduction in the number of microbes leads to amelioration of symptoms associated with the microbial presence.

As used herein, "water-insoluble" is used to describe a compound or complex having an octane:water partition coefficient (Log Kow) greater than zero (0). A water-insoluble substance, as used herein, has a water solubility of less than 15% w/w with respect to the weight of water.

As used herein, "water-soluble" is used to describe a compound or complex having an octane:water partition coefficient (Log Kow) less than zero (0). A water-soluble substance, as used herein, has a water solubility of greater than 15% w/w with respect to the weight of water.

Antimicrobial Compositions—Uncured

In many embodiments, an antimicrobial composition is described. The antimicrobial composition may include a polymerizable mixture comprising: at least one high Tg monomer and optionally a homopolymer thereof, wherein the homopolymer has a Tg of between about 40° C. and about 250° C.; at least one low Tg monomer and optionally a homopolymer thereof, wherein the homopolymer has a Tg of between about −70° C. and about 30° C.; an organic acid chelator, salt thereof, or combination thereof having a molecular weight less than about 400 g/mol; and a water-soluble plasticizer capable of solubilizing the organic acid chelator, or salt thereof, in an amount of at least about 100 g chelator per L of plasticizer at a temperature from about 20° C. to about 23° C. Upon polymerization, the polymerizable mixture forms a water-insoluble polymer composition comprising a copolymer derived from the at least one high Tg monomer and the at least one low Tg monomer.

In some embodiments, the antimicrobial composition may include one or more high Tg monomer. For example, the antimicrobial composition may include 1-5 high Tg monomers. In some embodiments, the antimicrobial composition may include one or more low Tg monomers. For example, the antimicrobial composition may include 1-5 low Tg monomers. In some embodiments, the antimicrobial composition may include 1 high Tg monomer and 1 low Tg monomer. In other embodiments, the antimicrobial composition may include 1 high Tg monomer and 2-3 low Tg monomers. The number and types of high Tg and low Tg monomers may be chosen based on ordinary knowledge in the art in order achieve the desired properties.

In some embodiments, the antimicrobial composition my include the at least one high Tg monomer present in an amount of about 1 part to about 50 parts by weight of the polymerizable mixture. For example, the at least one high Tg monomer may be present in parts by weight relative to the polymerizable mixture of about 1, 5, 10, 15, 20, 25, 30, 35, 40, 45, or 50, or a value between any of the preceding values, for example, between about 15 and about 30, between about 40 and about 50, or the like.

In some embodiments, the antimicrobial composition may include the at least one low Tg monomer present in an amount of about 50 parts to about 99 parts by weight of the polymerizable mixture. For example, the at least one low Tg monomer may be present in parts by weight relative to the polymerizable mixture of about 50, 55, 60, 65, 70, 75, 80, 85, 90, 95, or 99, or a value between any of the preceding values, for example, between about 60 and about 75, between about 50 and about 80, or the like.

In some embodiments, the polymerizable mixture may further include at least one mid Tg monomer and optionally a homopolymer thereof, wherein the homopolymer has a Tg of between about −20° C. and about 70° C. In some embodiments, the antimicrobial composition may include the at least one mid Tg monomer present in an amount of about 5 parts to about 50 parts by weight of the polymerizable mixture. For example, the at least one mid Tg monomer may be present in parts by weight relative to the polymerizable mixture of about 5, 10, 15, 20, 25, 30, 35, 40, 45, or 50, or a value between any of the preceding values, for example, between about 5 and about 10, between about 20 and 30, or the like.

In some embodiments, the antimicrobial composition may include the organic acid chelator, salt thereof, or combination thereof present in an amount of about 1 wt % to about 25 wt % with respect to the weight of the antimicrobial composition. For example, the organic acid chelator and/or salt thereof may be present in an amount in wt % with respect to the antimicrobial composition of about 1, 2, 3, 4, 5, 6, 7, 8, 9, 10, 15, 20, or 25, or a value between any of the preceding values, for example, between about 5 and about 10, between about 4 and about 20, or the like.

In some embodiments, the antimicrobial composition may further include water in an amount less than about 1 wt % with respect to the weight of the antimicrobial composition. For example, the antimicrobial composition may include water present in an amount in wt % with respect to the weight of the antimicrobial composition of about 1, 0.9, 0.8, 0.7, 0.6, 0.5, 0.4, 0.3, 0.2, 0.1, 0.05, 0.02, 0.01, or a wt % between any of the preceding values, for example, between about 0.02 and about 0.1, between about 0.05 and about 0.3, or the like. In some embodiments, the antimicrobial composition may include less than about 1 wt % water with respect to the weight of the antimicrobial composition.

In some embodiments, the antimicrobial composition may include the water-soluble plasticizer present in an amount of about 3 wt % to about 25 wt % with respect to the weight of the antimicrobial composition. For example, the water-soluble plasticizer may be present in an amount in wt % with respect to the weight of the antimicrobial composition of about 3, 4, 5, 6, 7, 8, 9, 10, 11, 12, 13, 14, 15, 20, or 25, or a value between any of the preceding values, for example, between about 10 and about 15, between about 8 and about 25, or the like. In some embodiments, the antimicrobial composition may include the water-soluble plasticizer present and organic acid chelator in an amount that it balances the antimicrobial and adhesive properties.

In some embodiments, the antimicrobial composition may further include one or more additional antimicrobial agent, for example, antimicrobial quaternary amine compound (e.g., benzalkonium chloride) or a salt thereof, a cationic surfactant (e.g. cetylpyridinium chloride, cetyltrimethylammonium bromide, etc.), polycationic compounds such as octenidine or a salt thereof, a biguanide compound (e.g., Chlorhexidine, polyhexamethylenebiguanide (PHMB) or a salt thereof, a (C6-C12) 1, 2-organic diol (e.g., 1,2-octanediol), an antimicrobial fatty acid monoester compound, and a combination of any two or more of the foregoing antimicrobial components. Preferred additional antimicrobials include an antimicrobial lipid, a phenolic antiseptic, a cationic antiseptic, iodine and/or an iodophor, a peroxide antiseptic, an antimicrobial natural oil, a C6-C12 alkane diol, silver, silver salts and complexes, silver oxide, copper, copper salts, or combinations thereof.

In some embodiments, the antimicrobial composition excludes antimicrobial compounds other than the organic acid chelator.

In some embodiments, the polymerizable mixture may further include a photoinitiator. The photoinitiator may be present in about 0.01 wt % to about 1 wt % with respect to the antimicrobial composition.

In some embodiments, the antimicrobial composition may further include one or more $C_{6-12}$ alkyl diol synergist, for example, 1,2-alkanediol, ethylhexylglycerin, fatty acid monoesters, alcohols, or the like.

In some embodiments, the antimicrobial composition may be characterized by a pH of about 3 to about 10. In some embodiments, the antimicrobial composition may be characterized by a pH of 3, 4, 5, 6, 7, 8, 9, or 10, or a value within a range between any of the preceding values, e.g., between about 4 and about 5, between about 6 and about 8, or the like. In other embodiments, the pH may be about 3 to about 12. Higher pH compositions may be afforded with the use of added base, e.g., NaOH, $KH_2PO_4$, $Na_2CO_3$, $NH_3$, NaClO, $Mg(OH)_2$, $NaHCO_3$, or the like.

In some embodiments, the antimicrobial composition may include one or more surfactants. In other embodiments, the antimicrobial composition may be essentially free of surfactants. In other embodiments, the antimicrobial composition may be free of surfactants, i.e., 0 wt % surfactants.

In some embodiments, the antimicrobial composition consists essentially of the at least one high Tg monomer, the at least one low Tg monomer, the organic acid chelator, and the water-soluble plasticizer.

In some embodiments, the antimicrobial composition consists essentially of at least one high Tg monomer, at least one low Tg monomer, at least one mid Tg monomer, an organic acid chelator, and a water-soluble plasticizer.

Polymerizable Mixture

High Tg Monomer

In some embodiments, any polymerizable mixture described herein may include at least one high Tg monomer having a Tg of between about 40° C. and about 250° C. For example, the at least one high Tg monomer may have a Tg in ° C. of about 40, 50, 60, 70, 80, 90, 100, 110, 120, 130, 140, 150, 160, 170, 180, 190, 200, 210, 220, 230, 240, or 250, or a Tg value between any of the preceding values, for example, between about 70 and about 100, between about 80 and about 250, between about 100 and about 230, or the like.

In some embodiments, the polymerizable mixture may include more than one high Tg monomer. For example, the monomer mixture may include 1-5 high Tg monomers described herein. In some embodiments, the polymerizable mixture may include one high Tg monomer described herein. In other embodiments, the polymerizable mixture may include two high Tg monomers described herein.

In some embodiments, the at least one high Tg monomer may be selected from compounds represented by Formula (I):

$$(R^{1a})(R^{2a})C{=}C(R^{3a}){-}X, \quad (I)$$

wherein:

X is selected from —C(O)OR$^{4a}$, —C(O)N(R$^{5a}$)(R$^{5a}$), —CN, —N(R$^{5a}$)—C(O)—R$^{6a}$, R$^{1a}$ is independently selected from —H, $C_{1-6}$ alkyl optionally substituted with one or more —OH, —$(CH_2)_n$—C(O)—R$^{7a}$, R$^{2a}$ is independently selected from —H, $C_{1-6}$ alkyl optionally substituted with one or more —OH, or R$^{2a}$ and R$^{4a}$, or R$^{2a}$ and R$^{5a}$, are taken together with the atoms to which they are attached to form a 5-6 membered heterocyclic ring, R$^{3a}$ is independently selected from —H, —OH, or $C_{1-6}$ alkyl optionally substituted with one or more —OH, R$^{4a}$ is —H, $C_{1-6}$ alkyl, or $C_{4-8}$ cycloalkyl optionally substituted with one or more $C_{1-4}$ alkyl, each R$^{5a}$ is independently —H or $C_{1-6}$ alkyl optionally substituted with one or more —OH, R$^{6a}$ is —H or $C_{1-6}$ alkyl, or R$^{5a}$ and R$^{6a}$ taken together with the atoms to which they are attached to form a 4-7 membered heterocyclic ring, R$^{7a}$ is —OR$^{8a}$ or —N(R$^{8a}$)(R$^{8a}$), R$^{7a}$ and R$^{4a}$, or R$^{7a}$ and R$^{5a}$, are taken together with the atoms to which they are attached to form a 5-6 membered heterocyclic ring;

each R$^{8}$ is independently selected from —H and $C_{1-6}$ alkyl; and n is an integer selected from 1-6.

In some embodiments, the at least one high Tg monomer may be selected from: acrylic acid, (alkyl)acrylic acids, (hydroxyalkyl)acrylic acids, alkyl acrylates, alkyl (alkyl) acrylates, alkyl (hydroxyalkyl)acrylates, hydroxy(alkyl) acrylates, hydroxy(alkyl) (alkyl)acrylates, hydroxy(alkyl) (hydroxyalkyl)acrylates, (hydroxyalkyl)acrylates, (alkyl) acrylamides, (hydroxyalkyl)acrylamides, α,β-unsaturated diacids, α,β-unsaturated diesters, α,β-unsaturated cyclic anhydrides, N-alkyl (alkyl)acrylamides, N-alkyl (hydroxyalkyl)acrylamides, N-hydroxyalkyl (alkyl)acrylamides, N-hydroxyalkyl (hydroxyalkyl)acrylamides, N,N-alkyl (alkyl)acrylamides, N,N-hydroxyalkyl (alkyl)acrylamides, N-alkyl, N-hydroxyalkyl (alkyl)acrylamides, N,N-alkyl (hydroxyalkyl)acrylamides, N,N-hydroxyalkyl (hydroxyalkyl) acrylamides, N-alkyl, N-hydroxyalkyl (hydroxyalkyl)acrylamides, (alkyl)acrylonitriles, N-vinyl lactams, and any combination thereof, or the like.

In some embodiments, the at least one high Tg monomer may be selected from: acrylic acid, methacrylic acid, acrylamide, acrylonitrile, methacrylonitrile, 2-hydroxyethyl acrylate, N-methyl acrylamide, N-vinyl pyrrolidone, N-vinyl caprolactam, maleic anhydride, isobornyl acrylate, itaconic acid, and any combination thereof.

In some embodiments, the at least one high Tg monomer may be acrylic acid.

Low Tg Monomer

In some embodiments, any polymerizable mixture described herein may include at least one low Tg monomer having a Tg of between about −60° C. and about 30° C. For example, the at least one low Tg monomer may have a low Tg in ° C. of about −60, −70, −60, −50, −40, −30, −20, −10, 0, 10, 20, or 30, or a Tg value between any of the preceding values, for example, between about −70 and about 0, between about −50 and 10, or the like.

In some embodiments, the polymerizable mixtures may include more than one low Tg monomer. For example, the polymerizable mixture may include 1-5 low Tg monomers described herein. In some embodiments, the polymerizable mixture includes one low Tg monomer described herein. In other embodiments, the polymerizable mixture includes two low Tg monomers described herein.

In some embodiments, the at least one low Tg monomer may be selected from compounds represented by Formula (II):

$$(R^{1b})(R^{2b})C{=}C(R^{3b}){-}Y, \quad (II)$$

wherein:

Y is —C(O)O—R$^{4b}$ or —OC(O)—($C_{1-6}$ alkyl),

R$^{1b}$ is independently selected from —H or $C_{1-18}$ alkyl,

R$^{2b}$ is independently selected from —H or $C_{1-18}$ alkyl,

R$^{3b}$ is independently selected from —H or $C_{1-18}$ alkyl, and

R$^{4b}$ is independently selected from —H or $C_{1-18}$ alkyl optionally substituted with one or more —OH and —CN, wherein at least one of R$^{1}$, R$^{2}$, R$^{3}$, or R$^{4}$ is $C_{4-18}$ alkyl.

In some embodiments, the at least one low Tg monomer is selected from a $C_{4-18}$ alkyl acrylate.

In some embodiments, the at least one low Tg monomer may be selected from: isooctyl acrylate, isononyl acrylate, isoamyl acrylate, isodecyl acrylate, 2-ethylhexyl acrylate, n-butyl acrylate, sec-butyl acrylate tert-butyl acrylate, butyl methacrylate, vinyl acetate, lauryl acrylate, octadecyl acrylate, 4-hydroxybutyl acrylate, and any combination thereof, or the like.

In some embodiments, the at least one low Tg monomer may be isooctyl acrylate.

Mid Tg Monomer

In some embodiments, any monomer mixture described herein may further include at least one mid Tg monomer having a Tg of between about −20° C. and about 70° C. For example, the at least one mid Tg monomer may have a mid Tg in ° C. of about −20, −10, 0, 10, 20, 30, 40, 50, 60, or 70 or a Tg value between any of the preceding values, for example, between about 20 and about 60, between about −10 and 30, or the like.

In some embodiments, the polymerizable mixture may include more than one mid Tg monomer described herein. For example, the polymerizable mixture may include 1-5 mid Tg monomers described herein. In some embodiments, the polymerizable mixture may include one mid Tg monomer described herein. In other embodiments, the polymerizable mixture may include two mid Tg monomers described herein.

In some embodiments, the at least one mid Tg monomer may be hydroxyethyl acrylate.

Monomer Combinations

In some embodiments, the polymerizable mixture may include the at least one high Tg monomer and the at least one low Tg monomer in a weight ratio of about 1:99 to about 20:80. For example, the weight ratio of the at least one high Tg monomer to the at least one low Tg monomer may be 1:99, 2:98, 3:97, 4:96, 5:95, 6:94, 7:93, 8:92, 9:91, 10:90, 11:89, 12:88, 13:87, 14:86, 15:85, 16:84, 17:83, 18:82, 19:81, or 20:80, or a ratio between any of the preceding values, for example, for example, between about 1:99 and about 5:95, between about 10:90 and about 15:85, or the like.

In some embodiments, the monomer mixture may include two low Tg monomers and one high Tg monomer.

In some embodiments, the polymerizable mixture may further include at least one mid Tg monomer present in a weight ratio with regard to the at least one high Tg monomer of about 30:70 to 70:30. For example, the weight ratio with regard to the mid to high Tg monomer to the at least one high Tg monomer may be: 30:70, 35:65, 40:60, 45:55, 50:50, 55:45, 60:40, 65:35, or 70:30, or ratio between any of the preceding values, for example, between 45:55 and about 65:35, between about 50:50 and about 60:40, or the like.

In some embodiments, the polymerizable mixture may further include at least one mid Tg monomer present in a weight ratio with regard to the at least one low Tg monomer of about 1:99 to about 20:80. For example, the weight ratio of the at least one mid Tg monomer to the at least one low Tg monomer may be 1:99, 2:98, 3:97, 4:96, 5:95, 6:94, 7:93, 8:92, 9:91, 10:90, 11:89, 12:88, 13:87, 14:86, 15:85, 16:84, 17:83, 18:82, 19:81, or 20:80, or a ratio between any of the preceding values, for example, for example, between about 1:99 and about 5:95, between about 10:90 and about 15:85, or the like.

In some embodiments, the polymerizable mixture may further include at least one mid Tg monomer present in a weight ratio with regard to the at least one high Tg monomer and the at least one low Tg monomer of about 5:1:95 to about 19:1:80. For example, the weight ratio with regard to the mid, high, and low Tg monomers may be 5:1:94, 6:1:93, 7:1:92, 8:1:91, 9:1:90, 10:1:89, 15:1:84, or 19:1:80, or a ratio between any of the preceding values, for example, between about 5:1:94 to about 10:1:89, or the like.

In some embodiments, the polymerizable mixture may include acrylic acid and isooctyl acrylate. The acrylic acid and isooctyl acrylate may be present in any amount or ratio described.

In some embodiments, the polymerizable mixture may include acrylic acid, isooctyl acrylate, and hydroxyethyl acrylate. The acrylic acid, isooctyl acrylate, and hydroxyethyl acrylate may be present in any amount or ratio described above.

In some embodiments, the polymerizable mixture may include isooctyl acrylate, 4-hydroxybutyl acrylate, acrylic acid, and hydroxyethyl acrylate in any amount or ratio described above.

Organic Acid Chelator

In many embodiments, the organic acid chelators or salts thereof described herein have antimicrobial properties. Without wishing to be bound by theory, it is presumed that the organic acid chelators or salts thereof are capable of chelating metal cations that are harbored within the phospholipid membrane of various organisms. Furthermore, it is believed that the sequestering of metal cations leads to cell lysis. In some embodiments, the sequestered metal cations are divalent metal cations. Example divalent metal cations include: $Zn^{2+}$, $Ca^{2+}$, $Mg^{2+}$, $Fe^{2+}$, or the like.

The organic chelator acid may additionally include heteroatom(s) selected from amines (—NR—), ethers (—O—), alcohols (—OH), esters (—$CO_2$—), acids (—$CO_2H$), amides (—C(O)NR—), amidines (—C(NR)NR—), oximes (—C(NOR)—), ureas (—NRC(O)NR—), carbamates (—NRC(O)O— or —OC(O)NR—), guanidines (—NRC(NR)NR—), thiol ethers (—S—), thiols (—SH), sulfoxides (—C(O)S— or —SC(O)—), sulfones (—$S(O)_2$—), or the like.

In several embodiments, the organic acid chelators described herein may be aliphatic. In some embodiments, the organic acid chelators may be aliphatic having no more than 10 carbons. In some embodiments, the organic acid chelators may be aliphatic having no more than 8 carbons. In some embodiments, the organic acid chelators may be aliphatic having no more than 6 carbons.

In other embodiments, the organic acid chelators described herein may be aromatic, i.e., include an aromatic group. In some embodiments, an organic acid chelator having an aromatic group may be an arylalkyl organic acid chelator. In some embodiments, the organic acid chelators may be aromatic having no more than 10 carbons. In some embodiments, the organic acid chelators may be aromatic having no more than 8 carbons. In some embodiments, the organic acid chelators may be aromatic having no more than 6 carbons.

In some embodiments, the organic acid chelators described herein may include 1 or more organic acid groups, e.g., —C(═O)OH, —P(═O)$(OH)_2$, —S(═O)$_2$OH, —S(═O)OH, a combination thereof, or the like, or salts thereof, e.g., —C(═O)O-M+, —P(═O)(OH)O-M+, —P(═O)(O—)$_2$ 2(M+), —S(O)$_2$O-M+, —S(O)O-M+, a combination thereof, or the like. In some embodiments, M+ may be selected from Li+, Na+, K+, Cs+, Ag+, or the like.

In some embodiments, the organic acid chelators described herein may include at least 2 organic acid groups, e.g., —C(O)OH, —P(O)$(OH)_2$, —S(O)$_2$OH, —S(O)OH, a combination thereof, or the like, or salts thereof, e.g., —C(═O)O-M+, —P(═O)(OH)O-M+, —P(═O)(O—)$_2$ 2(M+), —S(O)$_2$O-M+, —S(O)O-M+, a combination thereof, or the like. In some embodiments, M+ may be selected from Li+, Na+, K+, Cs+, Ag+, or the like.

In some embodiments, the organic acid chelators described herein may include at least 3 organic acid groups, e.g., —C(O)OH, —P(O)$(OH)_2$, —$S(O)_2$OH, —S(O)OH, a combination thereof, or the like, or salts thereof, e.g., —C(=O)O-M+, —P(=O)(OH)O-M+, —P(=O)$(O—)_2$ 2(M+), —S(O)2O-M+, —S(O)O-M+, a combination thereof, or the like. In some embodiments, M+ may be selected from Li+, Na+, K+, Cs+, Ag+, or the like.

In some embodiments, the organic acid chelator may include only —C(O)OH acid group(s) or salts thereof.

In some embodiments, the organic acid chelator may include 1 or more organic acid group or salt thereof as described above, and one or more electron-donor group, e.g., —OH, —O($C_{1-6}$ alkyl), =O, =NH, =N($C_{1-6}$ alkyl), —$NH_3$, —$NH_2$($C_{1-6}$ alkyl), —NH$(C_{1-6}$ alkyl$)_2$, and —N$(C_{1-6}$ alkyl$)_3$, wherein any of the $C_{1-6}$ may be substituted with —C(O)OH.

In some embodiments, the organic acid chelator may include 2 or more organic acid group or salt thereof as described above, and one or more electron-donor group, e.g., —OH, —O($C_{1-6}$ alkyl), =O, =NH, =N($C_{1-6}$ alkyl), —$NH_3$, —$NH_2$($C_{1-6}$ alkyl), —NH$(C_{1-6}$ alkyl$)_2$, and —N$(C_{1-6}$ alkyl$)_3$, wherein any of the $C_{1-6}$ may be substituted with —C(O)OH.

In some embodiments, the organic acid chelator includes at least two groups selected from —C(O)OH, —P(O)$(OH)_2$, —$S(O)_2$OH, —S(O)OH, —C(=O)O-M+, —P(=O)(OH)O-M+, —P(=O)$(O—)_2$ 2(M+), —$S(O)_2$O-M+, —S(O)O-M+, —OH, —O($C_{1-6}$ alkyl), =O, =NH, =N($C_{1-6}$ alkyl), —$NH_3$, —$NH_2$($C_{1-6}$ alkyl), —NH$(C_{1-6}$ alkyl$)_2$, and —N$(C_{1-6}$ alkyl$)_3$, wherein any of the $C_{1-6}$ may be substituted with —C(O)OH, and wherein at least one group may be selected from —C(O)OH, —P(O)$(OH)_2$, —$S(O)_2$OH, —S(O)OH, —C(=O)O-M+, —P(=O)(OH)O-M+, —P(=O)$(O—)_2$ 2(M+), —$S(O)_2$O-M+, —S(O)O-M+. Each M+ may be selected from Li+, Na+, K+, Cs+, Ag+, or the like.

In some embodiments, the heteroatoms (i.e., those having a lone pair of electrons) of at least two of the above groups are separated from one another by no more than 2-3 carbons. In some embodiments, the organic acid chelator may be an alpha-hydroxy acid or salt thereof.

In some embodiments, the organic acid chelator may be a beta-hydroxy acid or salt thereof.

In some embodiments, the organic acid chelator may be an alpha-amino acid or salt thereof.

In some embodiments, the organic acid chelator may be a beta-amino acid or salt thereof.

In many embodiments, the organic acid chelator or salt thereof may have a molecular weight less than about 400 g/mol. For example, the organic acid chelator or salt thereof may have a molecule weight in g/mol, of about 400, 375, 350, 325, 300, 275, 250, 225, 200, 175, 150, 125, 100, or 75, or a molecular weight between any of the preceding values, for example, between about 75 and about 200, between about 150 and 250, or the like.

In some embodiments, the organic acid chelator may be selected from citric acid, tartaric acid, malic acid, oxalic acid, maleic acid, malonic acid, ethylenediaminetetraacetic acid, aspartic acid, glutamic acid, a salt thereof, a combination thereof, or the like. In some embodiments, the organic acid chelator may be citric acid.

In some embodiments, the organic acid chelator or salt thereof may be present in an amount of about 1 wt % to about 25 wt % with respect to the weight of the antimicrobial composition. For example, the organic acid chelator or salt thereof may be present in an amount in wt % of about 1, 2, 3, 4, 5, 6, 7, 8, 9, 10, 12, 14, 16, 18, 20, 21, 22, 23, 24, or 25, or a wt % in a range between any of the preceding values, for example, between about 1 about 7, between about 3 and about 12, or the like.

Water-Soluble Plasticizers

In many ways, the plasticizers described herein act in a solubilizer capacity. The plasticizer may facilitate the migration of the organic acid chelator, or salt thereof, into the water-insoluble polymer. The solubilized organic acid chelator is made available to a surface, such as a skin surface, when the compositions described herein are contacted to the surface. The organic acid chelator is able to migrate from the water-insoluble polymer to the surface. Without a suitable plasticizer/solubilizer, the organic acid chelator remains an immobilized precipitate, which is largely unavailable to the surface.

In several embodiments, the water-soluble plasticizers described herein are not surfactants.

In some embodiments, the water-soluble plasticizer may have a molecular weight from about 50 g/mol to about 3,000 g/mol. For example, the water-soluble plasticizer may have a molecular weight, in g/mol, of about 50, 100, 200, 300, 400, 500, 600, 700, 800, 900, 1,000, 1,200, 1,400, 1,600, 1,800, 2,000, 2,200, 2,400, 2,600, 2,800 or 3,000 or a molecular weight between any of the preceding values, for example, between about 600 and about 1,000, between about 800 and about 2,200, or the like.

In some embodiments, the water-soluble plasticizers may be characterized by a water solubility of greater than 15% w/w with respect to the weight of water. The plasticizers may be characterized by a water solubility in % w/w with respect to the weight of water of greater than 15, 20, 25, 30, 35, 40, 45, 50, 55, 60, 65, 70, 75, 80, 85, 90, 95, 99, or a value between any of the preceding values, for example, between about 70 and about 90, between about 50 and about 80, or the like. In some embodiments, the water-soluble plasticizers may be characterized by a water solubility of greater than 80% w/w. In other embodiments, the water-soluble plasticizers may be 100% w/w soluble in water.

In some embodiments the water-soluble plasticizer may be selected from glycerol, a polyglycerol having 2-20 glycerin units, polyglycerols partially esterified with C1-C18 alkyl carboxylic acids having at least two free hydroxyl groups (e.g., hexaglycerol monolaurate, decaglycerol monolaurate, polyglyceryl-6 caprate, polyglyceryl-4 oleate, polyglyceryl-10 trilaurate and the like), polyethylene oxide, polyethylene glycol, polyethylene glycols initiated by any of the glycols discussed herein such as polyethylene glycol glyceryl ether, propylene glycol, dipropylene glycol, tripropylene glycol, 2-methyl 1,3 propane diol, sorbitol, dimethylisosorbide, pentaerythritol, trimethylol propane, ditrimethylolpropane, a random EO/PO copolymer or oligomer, a block EO/PO copolymer or oligomer, and a combination thereof.

In some embodiments, the water-soluble plasticizer may be selected from glycerol, polyglycerol-3, polyglycerol-4, polyglycerol-6, polyglycerol-10, diethylene glycol, polyethylene glycol of an average molecular weight from about 300 to about 800 g/mol, polyethylene glycol-3, polyethylene glycol-6, or a combination thereof.

In some embodiments, the water-soluble plasticizer may be present in an amount of about 3 wt % to about 35 wt % with respect to the weight of the antimicrobial composition. For example, the plasticizer may be present in an amount in wt % of about 3, 4, 5, 6, 7, 8, 9, 10, 12, 14, 16, 18, 20, 22, 24, 26, 28, 30 or 35, or a wt % in a range between any of the preceding values, for example, between about 5 about 10, between about 20 and about 26, or the like.

In some embodiments, the water-soluble plasticizer may be characterized by a Log Kow of less than 0.05. For example, the Log Kow of any suitable water-soluble plasticizer may be characterized by a Log Kow less than about 0.05, 0.02, 0.0, −0.02, 0.05, 0.08, −0.10, −0.20, −0.30, −0.40, −0.50, −0.60, −0.70, −0.80, −0.90, −1.0, −1.2, −1.4, −1.6, −1.8, −2.0, −2.2, −2.4, −2.6, −2.8, or −3.0, or a Log Kow value between any of the preceding values, for example, between about −1.40 and about ~1.80, between about −1.0 and about −2.0, or the like Chelator and Plasticizer In some embodiments, the water-soluble plasticizer may be glycerin and the organic chelator compound may be citric acid or a salt thereof.

In some embodiments, the water-soluble plasticizer may be glycerin and the organic chelator compound may be tartaric acid or a salt thereof.

In some embodiments, the water-soluble plasticizer may be glycerin and the organic chelator compound may be maleic acid or a salt thereof.

In some embodiments, the water-soluble plasticizer may be glycerin and the organic chelator compound may be ethylenediaminetetraacetic acid or a salt thereof.

In some embodiments, the water-soluble plasticizer may be glycerin and the organic chelator compound may be selected from citric acid, tartaric acid, maleic acid, ethylenediamine tetraacteric acid, or a salt thereof, wherein the antimicrobial composition may further include a base buffer, e.g., NaOH, $Na_2CO_3$, $NH_3$, NaClO, $Mg(OH)_2$, $NaHCO_3$, and $KH_2PO_4$.

In some embodiments, the water-soluble plasticizer may be polyethylene glycol and the organic acid chelator may be citric acid or a salt thereof.

In some embodiments, the water-soluble plasticizer may be polyethylene glycol and the organic acid chelator may be tartaric acid or a salt thereof.

In some embodiments, a water-soluble plasticizer described herein and an organic acid chelator or salt thereof described herein may be present in a weight ratio of about 1:1 to about 8:1. For example, the weight ratio may be about 1:1, 1.5:1, 2:1, 2.5:1, 3:1, 3.5:1, 4:1, 4.5:1, 5:1, 5.5:1, 6:1, 6.5:1, 7:1, 7.5:1, or 8:1, or a weight ratio between a range of any of the preceding values, for example, between about 2:1 and about 4:1, between about 3:1 and about 7:1, or the like.

In some embodiments, a water-soluble plasticizer and an organic acid chelator or salt thereof do not form a covalent complex. For example, a water-soluble plasticizer such as glycerin and an organic acid chelator such as citric acid, do not esterify to form a glyceryl citrate so that acids groups are available to provide antimicrobial properties.

Photoinitiators

In some embodiments, the photoinitiator may be a Norrish Type I photoinitiator. Norrish Type I photoinitiators are homolytically cleaved into two radical fragments upon irradiation with UV-light. These radicals then initiate polymerization of the monomer units. The photoinitiator used herein may be any Norrish Type I photoinitiator known to those skilled in the art.

Norrish Type II photoinitiators on the other hand require a hydrogen donor, e.g., amine synergist, in order for UV-irradiation to initiate radical formation. As shown below, Norrish Type I photoinitiators successfully cure the one or more (meth)acrylate monomers, whereas Norrish Type II photoinitiators do not.

In some embodiments, the photoinitiator may be selected from a group under the trade name Irgacure® or Darocur®, e.g., Irgacure® 651, Irgacure® 819, Irgacure® 184, Irgacure® 2959, Darocur® 1173, or the like. These photoinitiators each have a benzoyl fragment that produces a benzyol radical upon irradiation with UV-light.

In some embodiments, the photoinitiator may be 2,2-dimethoxy-2-phenylacetophenone.

In some embodiments, the photoinitiator may be bis(2,4,6-trimethylbenzoyl)-phenylphosphineoxide.

In some embodiments, the photoinitiator may be 1-hydroxycyclohexyl phenyl ketone.

In some embodiments, the photoinitiator may be 2-hydroxy-4'-(2-hydroxyethoxy)-2-methylpropiophenone.

Antimicrobial Compositions—Cured

In many embodiments, an antimicrobial composition is described. The antimicrobial composition may include a water-insoluble polymer composition comprising a co-polymer derived from a polymerizable mixture comprising at least one high Tg monomer and optionally a homopolymer thereof, wherein the homopolymer has a Tg of between about 40° C. and about 250° C., and at least one low Tg monomer and optionally a homopolymer thereof, wherein the homopolymer has a Tg of between about −70° C. and about 30° C.; an organic acid chelator, salt thereof, or combination thereof having a molecular weight less than about 400 g/mol; and a water-soluble plasticizer capable of solubilizing the organic acid chelator, or salt thereof, in an amount of at least about 100 g chelator per L of plasticizer at a temperature from about 20° C. to about 23° C. The antimicrobial composition may be a pressure-sensitive adhesive.

In many embodiments, the polymerizable mixture may include any monomer combination described above. In many embodiments, any monomer or combination of monomer may be present in amount(s) described above.

In many embodiments, the organic acid chelator may include any organic acid chelator or salt thereof described above. In many embodiments, the organic acid chelator may be present in any amount described above.

In many embodiments, the water-soluble plasticizer may include any water-soluble plasticizer described above. In many embodiments, the water-soluble plasticizer may be present in any amount described above.

In many embodiments, the (cured) antimicrobial composition may include one or more of the additional features described above for the (uncured) antimicrobial composition. The (cured) antimicrobial composition may be prepared from the (uncured) antimicrobial composition described above.

In some embodiments, the antimicrobial composition may be essentially free of water, i.e., less than about 0.1 wt % water.

Water-Insoluble Polymer

In many embodiments, the water-insoluble polymer composition may be derived from any polymerizable mixture described herein.

In some embodiments, the water-insoluble polymer may be a random polymer.

In some embodiments, the water-insoluble polymer may be a block co-polymer.

In some embodiments, the water-insoluble polymer may include a random polymer and a block co-polymer.

In some embodiments, the water-insoluble polymer may include randomly polymerized portions and block co-polymerized portions.

In some embodiments, the water-insoluble polymer may include one or more homopolymer.

In some embodiments, the water-insoluble polymer may have a Log Kow of greater than 0. For example, the water-insoluble polymer may have a Log Kow of greater than 0, 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 5.0, 6.0, 7.0, or 8.0, or a value between any of the preceding values, for example, between about 2.0 and about 4.0, between about 2.8 and about 6.0, or the like.

In some embodiments, the water-insoluble polymer may be soluble in water in an amount less than about 15% w/w with respect to the weight of the water. The water-insoluble polymer may be soluble in water, in % w/w, in an amount less than about 15, 14, 13, 12, 11, 10, 9, 8, 7, 6, 5, 4, 3, 2, or 1, or within a range of any of the preceding values, for example, between about 10 and about 15, between about 5 and about 8, or the like.

In some embodiments, the water-insoluble polymer may be a polyacid, i.e., derived from monomers having one or more —C(O)OH, —P(O)$(OH)_2$, —S$(O)_2$OH, —S(O)OH, or the like.

In some embodiments, the water-insoluble polymer may be a polyacid consisting essentially of a hydrocarbon backbone and pendant organic acid groups, e.g., —C(O)OH, —P(O)$(OH)_2$, —S$(O)_2$OH, —S(O)OH, or the like.

In some embodiments, the water-insoluble polymer may be a polyacid polyester.

In some embodiments, the water-insoluble polymer may be a polyacid polyester consisting essentially of a hydrocarbon backbone and pendant organic acid groups, e.g., —C(O)OH, —P(O)$(OH)_2$, —S$(O)_2$OH, —S(O)OH, or the like, and pendant organic ester groups, e.g., —C(O)O($C_{1-6}$ alkyl).

Antimicrobial Articles

In many embodiments, an antimicrobial article is described. The antimicrobial article may include a substrate including a first surface and a second surface opposite the first surface. The antimicrobial article may include an antimicrobial composition described herein disposed on the first surface.

In some embodiments, the substrate may be a polymeric film. The polymeric film may be woven or nonwoven.

In some embodiments, the antimicrobial article may further include a release liner in contact with the antimicrobial composition.

In some embodiments, the antimicrobial article may further include a delivery liner in contact with the second surface. The delivery liner may cover at least a portion of the second surface and be removable or permanently adhered to the second surface. The delivery liner may assist a user in the application of the substrate to a surface.

In some embodiments, the antimicrobial composition may be any cured antimicrobial composition described herein.

In some embodiments, the antimicrobial article may be in the form of a sheet or a roll.

In some embodiments, the antimicrobial article may be configured in various shapes, including custom shapes for fitting over contoured surfaces. The antimicrobial article may be in the shape of any wound bandage known in the art.

In some embodiments, the antimicrobial article is a wound dressing.

In some embodiments, the antimicrobial article is a surgical drape.

In some embodiments, the antimicrobial article is an intravenous dressing.

In some embodiments, the antimicrobial article is a tape or wrap.

Methods of Preparing an Antimicrobial Pressure-Sensitive Adhesive

In several embodiments, a method for preparing an antimicrobial pressure-sensitive adhesive described herein is described. The method may include providing an antimicrobial composition (uncured) described herein and a photoinitiator described herein. The method may include irradiating the antimicrobial composition and photoinitiator with electromagnetic radiation at a wavelength of about 280 nm to about 500 nm for a period to at least partially cure the antimicrobial composition.

In many embodiments, the antimicrobial pressure-sensitive adhesive may be any (cured or partially cured) antimicrobial composition described herein.

In some embodiments, a completely cured water-insoluble polymer may include less than 5 wt %, less than 4 wt %, less than 3 wt %, less than 2 wt %, or less than 1 wt % of unreacted monomers.

In some embodiments, a partially-cured water-insoluble polymer may include more than 5 wt %, more than 10 wt %, more than 20 wt %, more than 30 wt %, more than 40 wt %, more than 50 wt %, more than 60 wt %, more than 65 wt %, more than 70 wt %, more than 80 wt %, more than 90 wt % of unreacted monomers. In some embodiments, a partially-cured water-insoluble polymer may include up to about 95 wt % of unreacted monomers.

In some embodiments, the method may further include contacting the antimicrobial composition to the photoinitiator.

In some embodiments, the method may further include contacting the antimicrobial composition and the photoinitiator to a substrate prior to irradiating.

In some embodiments, the irradiating may be at a wavelength of about 280, 290, 300, 310, 320, 330, 340, 350, 360, 370, 380, 390, 400, 410, 420, 430, 440, 450, 460, 470, 480, 490, or 500, of at a wavelength between any of the preceding values, for example, between about 380 and about 450, between about 300 and about 400, or the like.

In some embodiments, the period may be from about 3 seconds to about 60 minutes. For example, the period may be in minutes of about 0.05, 0.1, 0.2, 0.3, 0.4, 0.5, 0.6, 0.7, 0.8, 0.9, 1.0, 5.0, 10, 15, 20, 25, 30, 35, 40, 45, 50, 55, or 60, or a value within a range of any of the preceding values, for example between about 1.0 and about 5.0, between about 0.5 and about 40, or the like.

In some embodiments, the period may be selected to partially cure the antimicrobial composition. In some embodiments, the partially cured antimicrobial composition may be cured to about 5 wt % to about 70 wt % of the monomers. The weight percentage of monomers that are cured in a partially-cured water-insoluble polymer mixture may be about 5, 10, 15, 20, 25, 30, 35, 40, 45, 50, 60, 65, or 70, or a value within a range between any of the preceding values, for example, between about 30 and about 50, between about 20 and about 40, or the like.

In other embodiments, the period may be selected to fully cure the antimicrobial composition to provide the antimicrobial pressure-sensitive adhesive.

Methods of Preparing an Antimicrobial Pressure-Sensitive Adhesive

In several embodiments, a method for preparing an antimicrobial pressure-sensitive adhesive is described. The method may include providing an antimicrobial composition described herein and a photoinitiator described herein. The method may include irradiating the antimicrobial composition and the photoinitiator with electromagnetic radiation at a wavelength of about 280 to 500 nanometers at an average light intensity of about 0.01 to about 20 milliwatts per centimeter squared ($mW/cm^2$), wherein the irradiating is effective to polymerize about 5 wt % to about 70 wt % of the antimicrobial composition to provide a polymeric composition. The method may include irradiating the polymeric composition with electromagnetic radiation at a wavelength of about 280 to 500 nm wavelength at an average light intensity of greater than about 20 $mW/cm^2$ to provide the antimicrobial pressure-sensitive adhesive.

In some embodiments, the antimicrobial composition may be essentially free of solvent(s), e.g., halogenated organic solvents, e.g., methylene chloride, chloroform, trichloroethylene; ethereal organic solvents, e.g., diethyl ether, dimethoxy ethane, tetrahydrofuran, hydrocarbon organic solvents, e.g., pentane, hexane, toluene, benzene, xylene; and other volatile organic solvents, e.g., $C_{1-6}$ alcohols, ethyl acetate, acetonitrile; and the like.

In some embodiments, the antimicrobial composition may be partially polymerized prior to the irradiating(s).

In some embodiments, each irradiating may be independently selected from a wavelength in nm of about 280, 290, 300, 310, 320, 330, 340, 350, 360, 370, 380, 390, 400, 410, 420, 430, 440, 450, 460, 470, 480, 490 or 500, or a value within range between any of the preceding values, for example, between about 300 and about 380, between about 320 and about 440, or the like.

In some embodiments, irradiating the antimicrobial composition may be at any one of the preceding wavelength values at an average light intensity in $mW/cm^2$ of about 0.01, 0.05, 0.1, 0.2, 0.3, 0.4, 0.5, 1.0, 2.0, 4.0, 6.0, 8.0, 10.0, 12.0, 14.0, 16.0, 18.0, or 20.0, or a value within a range between any of the preceding values, for example, between about 0.1 and about 2.0, between about 6.0 and about 12.0, or the like.

In some embodiments, the irradiating is effective to polymerize the antimicrobial composition in wt % of about 5, 10, 15, 20, 25, 30, 35, 40, 45, 50, 55, 60, 65, or 70, or a value within a range between any of the preceding values, for example, between about 25 and about 30, between about 10 and about 50, or the like.

In some embodiments, irradiating the polymeric composition may be at nay one of the preceding wavelength values at an average light intensity in $mW/cm^2$ of no greater than about 20, 19, 18, 17, 16, 15, 14, 13, 12, 11, 10, 9, 8, 7, 6, 5, 4, 3, 2, 1, 0.05, 0.02, or 0.01, or a value within a range between any of the preceding values, for example, between about 1 and about 7, between about 10 and about 15, or the like.

Methods for Disrupting Biofilm

In several embodiments, a method for preventing or disrupting a biofilm on a surface is described. The method may include providing an antimicrobial article described herein and contacting the antimicrobial article to the surface for a period, wherein the contacting is effective to prevent the formation or growth of a biofilm or disrupt an existing biofilm on the surface.

In other embodiments, the method may include providing an antimicrobial composition described herein in lieu of the antimicrobial article, and contacting the antimicrobial composition (cured) to the surface for a period.

In some embodiments, the surface is a skin or tissue. In some embodiments, the skin or tissue is mammalian skin or tissue. In some embodiments, the skin or tissue is wounded or otherwise damaged. In some embodiments, the tissues may be selected from mucosal tissues, chronic wounds, acute wounds, burns, or the like.

In other embodiments, the surface is a medical surface, for example, surgical devices (e.g., scalpel, scissors, blades, forceps, drapes, or the like), medical devices (e.g., catheters, stents, artificial joints, dental implants, or the like), floor tiles, countertops, tubs, dishes, gloves, swabs, cloth, sponges, foams, nonwovens, and paper products.

In some embodiments, the antimicrobial articles (or antimicrobial compositions) may be effective at disrupting biofilms of various microorganisms types. For example, Gram positive bacteria, Gram negative bacteria, fungi, protozoa, mycoplasma, yeast viruses, lipid-enveloped viruses, or the like. For example, the antimicrobial compositions or articles made therefrom may reduce the numbers of *Staphylococcus* spp., *Streptococcus* spp., *Pseudomonas* spp., *Enterococcus* spp., *Escherichia* spp., *Aspergillus* spp., *Fusarium* spp., *Candida* spp., and the like. For example, the antimicrobial compositions or articles made therefrom may reduce the numbers of *Staphylococcus aureus*, methicillin-resistant *Staphylococcus aureus* (MRSA), *Staphylococcus epidermidis, Streptococcus pneumoniae, Enterococcus faecalis*, vancomycin-resistant *Enterococcus* (VRE), *Pseudomonas aeruginosa, Esherichia coli, Aspergillus niger, Aspergillus fumigatus, Aspergillus clavatus, Fusarium solani, Fusarium oxysporum, Fusarium chlamydosporum, Candida albicans, Candid glabrata, Candida krusei*, and the like.

In some embodiments, the antimicrobial article (or antimicrobial composition) may contact the surface for a period in minutes of about 30, 60, 90, 120, 150, 180, or 210 or a value between any of the preceding values, for example, between about 30 and about 120, between about 90 and about 180, or the like. In other embodiments, the antimicrobial article may contact the surface for a period in hours of greater than about 1, 2, 3, 4, 5, 12, or 24, or a value between any of the preceding values, for example between about 2 and about 5, between about 12 and about 24, or the like. In some embodiments, the antimicrobial article may contact the surface for a period in days of about 1, 2, 3, 4, 5, 6, or 7, or a value between any of the preceding values, for example, between about 1 and about 2, between about 2 and about 5, or the like.

Methods for Reducing Microorganisms

In several embodiments, a method for reducing a number of microorganisms on a surface is described. The method may include providing an antimicrobial article described herein and contacting the antimicrobial article to the surface for a period, wherein the contacting is effective to reduce the number of microorganisms within an area of the surface contacted by the antimicrobial article.

In other embodiments, the method may include providing an antimicrobial composition described herein in lieu of the antimicrobial article, and contacting the antimicrobial composition to the surface for a period.

In some embodiments, the antimicrobial articles (or antimicrobial compositions) may be effective at reducing the number of various microorganisms described herein.

In some embodiments, the surface may be any a skin surface, a utensil surface, a surface prepped to hold utensils, or any other surface in need of disinfection such as other surfaces described herein.

In some embodiments, the antimicrobial article (or antimicrobial composition) may contact the surface for a period in minutes of about 30, 60, 90, 120, 150, 180, or 210 or a value between any of the preceding values, for example, between about 30 and about 120, between about 90 and about 180, or the like. In other embodiments, the antimicrobial article may contact the surface for a period in hours of greater than about 1, 2, 3, 4, 5, 12, or 24, or a value between any of the preceding values, for example between about 2 and about 5, between about 12 and about 24, or the like. In some embodiments, the antimicrobial article may contact the surface for a period in days of about 1, 2, 3, 4, 5, 6, or 7, or a value between any of the preceding values, for example, between about 1 and about 2, between about 2 and about 5, or the like.

Methods for Treating Infections

In several embodiments, a method for treating or preventing an infection is described. The method may include providing an antimicrobial article described herein and contacting the antimicrobial article to a surface in need of disinfecting for a period, wherein the contacting is effective to ameliorate one or more symptom of the infection, and wherein the contacting is effective to prevent the onset of an infection characterized by one or more symptoms of infection.

In some embodiments, a symptom of infection may include, for example, redness, swelling, inflammation, increased local or bodily temperature, presence of pus, a combination thereof, or the like.

Kits

In many embodiments, a kit is described. The kit may include any antimicrobial article described herein and a set of instructions directing a user to perform the method steps for reducing the number of microorganisms on a surface described herein or disrupting a biofilm on a surface described herein.

EXAMPLES

Objects and advantages of this disclosure are further illustrated by the following examples, but the particular materials and amounts thereof recited in these examples, as well as other conditions and details, should not be construed to unduly limit this disclosure. These examples are merely for illustrative purposes only and are not meant to be limiting on the scope of the appended claims.

| Materials | Supplier |
|---|---|
| Isooctyl acrylate (IOA) | BASF Corporation, Florham Park, NJ |
| Acrylic acid (AA) | BASF Corporation, Florham Park, NJ |
| 2-Dimethoxy-2-phenylacetophenone, a photoinitiator available under the trade designation IRGACURE 651 | BASF Corporation, Florham Park, NJ |
| Sodium Citrate (trisodium salt dihydrate) | Sigma Aldrich, St. Louis, MO |
| Citric Acid Monohydrate | Sigma Aldrich, St. Louis, MO |
| Glycerol | Cargill Corporation, Wayzata, MN |

Mixture A: Procedure for Dissolving Citric Acid in Glycerol

Fifteen grams (g) of citric acid was added to a 240 mL glass jar containing 100 g of glycerol at room temperature. The jar was sealed and put on a rolling mixer for 60-70 hours until a clear solution was obtained. The solution is referred to as Mixture A.

Mixture B: Procedure for Mixing Citric Acid and Sodium Hydroxide in Glycerol

To a 240 mL glass jar were added 26.5 g citric acid, 3.5 g sodium hydroxide, and 70 g of glycerol at room temperature. The jar was sealed and put on a rolling mixer for 60-70 hours until a clear solution was obtained. The solution is referred to as Mixture B.

Procedure for Making Pressure Sensitive Adhesives

Mixture C (without any Organic Acid Chelator and Glycerol)

A pressure sensitive adhesive precursor composition was prepared by combining 95 g IOA, 5 g AA and 0.05 g IRGACURE 651. This composition was partially polymerized under a nitrogen atmosphere by exposure to low intensity (UV-A) ultraviolet radiation to provide a cloudy, coatable, viscous syrup. A rectangular form approximately 100 mm by 150 mm and having depth of 1-3 mm was created by placing 3M VHB™ tape on a release liner. The cloudy syrup was poured into this rectangle form, covered with an additional sheet of release liner, and placed underneath rapid-start light bulbs for 30 minutes to 1 hour under a nitrogen atmosphere. The resulting cured adhesive was further tested for zone of inhibition and quantitative tack using tack tester.

Mixture D (without any Organic Acid Chelator and Glycerol)

A pressure sensitive adhesive precursor composition was prepared by combining 99 g IOA, 1 g AA and 0.05 g IRGACURE 651. This composition was partially polymerized under a nitrogen atmosphere by exposure to low intensity (UV-A) ultraviolet radiation to provide a cloudy, coatable, viscous syrup. A rectangular form approximately 100 mm by 150 mm and having depth of 1-3 mm was created by placing 3M VHB™ tape on a release liner. The cloudy syrup was poured into this rectangle form, covered with an additional sheet of release liner, and placed underneath rapid-start light bulbs for 30 minutes to 1 hour under a nitrogen atmosphere. The resulting cured adhesive was further tested for zone of inhibition and quantitative tack using tack tester.

Example 1

A pressure sensitive adhesive precursor composition was prepared by combining 80 g IOA, 20 g AA, 0.05 g IRGACURE 651, and 11.5 g of Mixture A. This composition was partially polymerized under a nitrogen atmosphere by exposure to low intensity (UV-A) ultraviolet radiation to provide a cloudy, coatable, viscous syrup. The syrup was observed for the next three days and showed no settling or separation.

A rectangular form approximately 100 mm by 150 mm and having depth of 1-3 mm was created by placing 3M VHB™ tape on a release liner. The cloudy syrup was poured into this rectangle form, covered with an additional sheet of release liner, and placed underneath rapid-start light bulbs for 30 minutes to 1 hour under a nitrogen atmosphere. The resulting cured adhesive was further tested for zone of inhibition and quantitative tack using tack tester.

Example 2

A pressure sensitive adhesive precursor composition was prepared by combining 80 g IOA, 20 g AA, 0.05 g of IRGACURE 651, and 2 g citric acid. The syrup was partially polymerized under a nitrogen atmosphere by exposure to low intensity (UV-A) ultraviolet radiation. The partially cured syrup that was obtained contained precipitated citric acid particles.

Example 3

A pressure sensitive adhesive precursor composition was prepared by combining 90 gms of mixture C syrup which was already partially polymerized and 10 g of Mixture B and mixed on roller overnight.

A rectangular form with dimensions of approximately 100 mm by 150 mm and a depth of 1-3 mm was created by placing 3M VHB™ tape on a release liner. The cloudy syrup was poured into this rectangle form, covered with an additional sheet of release liner, and placed underneath rapid-start light bulbs for 30 minutes to 1 hour in a nitrogen atmosphere. The resulting adhesive was tacky to the touch.

Example 4

A pressure sensitive adhesive precursor composition was prepared by combining 80 gms of mixture C syrup which was already partially polymerized and 20 g of Mixture B and mixed on roller overnight. A rectangular form approximately 100 mm by 150 mm and having depth of 1-3 mm was created by placing 3M VHB™ tape on a release liner. The cloudy syrup was poured into this rectangle form, covered with an additional sheet of release liner, and placed underneath rapid start light bulbs for 30 minutes to 1 hour in a nitrogen atmosphere. The resulting cured adhesive was further tested for zone of inhibition and quantitative tack using tack tester.

Example 5

A pressure sensitive adhesive precursor composition was prepared by combining 65 gms of mixture C syrup which was already partially polymerized and 35 g of Mixture B and mixed on roller overnight. A rectangular form approximately 100 mm by 150 mm and having depth of 1-3 mm was created by placing 3M VHB™ tape on a release liner. The cloudy adhesive mixture was poured into this rectangle form, covered with an additional sheet of release liner, and placed underneath rapid start light bulbs for 30 minutes to 1 hour in a nitrogen atmosphere. The resulting cured adhesive was further tested for zone of inhibition and quantitative tack using tack tester.

Example 6

A pressure sensitive adhesive precursor composition was prepared by combining 90 gms of mixture D syrup which was already partially polymerized and 10 g of Mixture B and mixed on roller overnight. A rectangular form with dimensions of approximately 100 mm by 150 mm and a depth of 1-3 mm was created by placing 3M VHB™ tape on a release liner. The cloudy adhesive mixture was poured into this rectangle form, covered with an additional sheet of release liner, and placed underneath rapid-start light bulbs for 30 minutes to 1 hour in a nitrogen atmosphere. The resulting cured adhesive was further tested for zone of inhibition and quantitative tack using tack tester.

Antimicrobial Testing Using Zone of Inhibition

A Zone of Inhibition Test, also called a Kirby-Bauer Test, is a qualitative method to measure antimicrobial resistance. Zone of inhibition testing was conducted using the cured adhesive of Example 1. A *P. aeruginosa* culture was streaked onto trypic soy agar and incubating at 35° C. overnight. A bacteria suspension was prepared in phosphate buffered water (PBW) to a density approximately 8 logs using a McFarland turbidity standard 0.5 and further diluted 1:1000 in PBW. The diluted suspension was streaked onto the surface of Mueller Hinton agar and allowed to dry in order to form a lawn of bacteria. Samples of the cured adhesive of Example 1 were placed on the surface of the agar and the plates were put in a 35° C. incubator overnight. Afterward, the plates were examined and a zone of inhibition was observed, indicating *P. aeruginosa* is susceptible to the cured adhesive. The values are reported in Table 1 in 'mm' as the circular zone formed around the sample. For example, value 6 mm represents 6 mm distance from the edge of circular sample.

Tack Testing

Tack testing was done by using TA-XT2 texture analyzer. Glass micro slides (VWR cat No. 48312-002) was used to which double sided adhesive tape (3M™ Medical Tape 1577, Double Sided Differential Adhesive Polyester, 60 #Liner, Configurable, Synthetic Rubber Adhesive/Tackified Acrylic Adhesive) was attached to which adhesive was attached. Force 10.0 gms distance 10 mm, test speed 2 mm/seconds. The work of adhesion was recorded and represented in Table 1.

TABLE 1

Zone of inhibition and work of adhesion.

| Examples | *P. aeruginosa* Zone of inhibition (mm) | Work of adhesion g · s |
|---|---|---|
| Mixture D | 3 | 101.2 |
| 1 | 6 | 383.7 |
| 4 | 6 | 121.5 |
| 5 | 9 | 10.7 |
| 6 | 3 | 81.47 |

Example 1 provided the highest adhesion and a desirable inhibition. A significant loss in adhesion (example 5) was observed with greater amounts of glycerol and citric acid; however, greater amounts of glycerol and citric acid afforded the highest antimicrobial properties.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. An antimicrobial pressure sensitive adhesive precursor composition comprising:

a polymerizable mixture or a partially polymerized composition thereof, the polymerizable mixture comprising:

at least one high Tg monomer capable of forming a homopolymer having a Tg of between about 40° C. and about 250° C.;

at least one low Tg monomer capable of forming a homopolymer having a Tg of between about −70° C. and about 30° C.; and a photoinitiator;

wherein upon polymerization, the polymerizable mixture forms a water-insoluble polymer composition comprising a copolymer derived from the at least one high Tg monomer and the at least one low Tg monomer;

a chelator having a molecular weight less than about 400 g/mol, which is an organic acid chelator, a salt thereof, or combinations thereof; and a water-soluble plasticizer capable of solubilizing the chelator in an amount of at least about 100 g chelator per L of plasticizer at a temperature from about 20° C. to about 23° C.

2. The antimicrobial pressure sensitive adhesive precursor composition of claim 1, wherein the at least one high Tg monomer is represented by Formula (I):

$$(R^{1a})(R^{2a})C{=}C(R^{3a}){-}X, \quad (I)$$

wherein:

X is —C(O)OR$^{4a}$, —C(O)N(R$^{5a}$)(R$^{5a}$), —CN, or —N(R$^{5a}$)—C(O)—R$^{6a}$;

R$^{1a}$ is independently —H, $C_{1-6}$ alkyl optionally substituted with one or more —OH, or —$(CH_2)_n$—C(O)R$^{7a}$;

R$^{2a}$ is independently —H, or $C_{1-6}$ alkyl optionally substituted with one or more —OH; or R$^{2a}$ and R$^{4a}$, or R$^{2a}$ and R$^{5a}$, are taken together with the atoms to which they are attached to form a 5-6 membered heterocyclic ring;

R$^{3a}$ is independently —H, —OH, or $C_{1-6}$ alkyl optionally substituted with one or more —OH;

R$^{4a}$ is —H, $C_{1-6}$ alkyl, or $C_{4-8}$ cycloalkyl optionally substituted with one or more $C_{1-4}$ alkyl;

each R$^{5a}$ is independently —H or $C_{1-6}$ alkyl optionally substituted with one or more —OH;

R$^{6a}$ is —H or $C_{1-6}$ alky; or R$^{5a}$ and R$^{6a}$ taken together with the atoms to which they are attached to form a 4-7 membered heterocyclic ring;

R$^{7a}$ is —OR$^{8a}$ or —N(R$^{8a}$)(R$^{8a}$); or R$^{7a}$ and R$^{4a}$, or R$^{7a}$ and R$^{5a}$, are taken together with the atoms to which they are attached to form a 5-6 membered heterocyclic ring;

each R$^{8}$ is independently —H or $C_{1-6}$ alkyl; and n is an integer selected from 1-6.

3. The antimicrobial pressure sensitive adhesive precursor composition of claim 1, the at least one low Tg monomer is represented by Formula (II):

$$(R^{1b})(R^{2b})C{=}C(R^{3b}){-}Y \quad (II)$$

wherein:

Y is —C(O)O—R$^{4b}$ or —OC(O)—($C_{1-6}$ alkyl);

R$^{1b}$ is independently —H or $C_{1-18}$ alkyl;

R$^{2b}$ is independently —H or $C_{1-18}$ alkyl;

R$^{3b}$ is independently —H or $C_{1-18}$ alkyl; and

R$^{4b}$ is independently —H or $C_{1-18}$ alkyl optionally substituted with one or more of —OH and —CN; and wherein at least one of R$^{1}$ R$^{2}$, R$^{3}$, or R$^{4}$ is $C_{4-18}$ alkyl.

4. The antimicrobial pressure sensitive adhesive precursor composition of claim 1, wherein:

the at least one high Tg monomer and the at least one low Tg monomer are present in the polymerizable mixture at a weight ratio of about 1:99 to about 20:80.

5. The antimicrobial pressure sensitive adhesive precursor composition of claim 1, wherein the polymerizable mixture comprises isooctyl acrylate as a low Tg monomer, 4-hydroxybutyl acrylate as a low Tg monomer, acrylic acid as a high Tg monomer, or a combination thereof.

6. The antimicrobial pressure sensitive adhesive precursor composition of claim 1, wherein the polymerizable mixture further comprises at least one mid Tg monomer capable of forming a homopolymer having a Tg of between about −20° C. and about 70° C.

7. The antimicrobial pressure sensitive adhesive precursor composition of claim 6, wherein the at least one mid Tg monomer, the at least one high Tg monomer, and the at least one low Tg monomer are present in the polymerizable mixture at a weight ratio of about 5:1:95 to about 19:1:80.

8. The antimicrobial pressure sensitive adhesive precursor composition of claim 6, wherein the polymerizable mixture comprises hydroxyethyl acrylate as a mid Tg monomer.

9. The antimicrobial pressure sensitive adhesive precursor composition of claim 6, wherein the polymerizable mixture comprises isooctyl acrylate as a low Tg monomer, 4-hydroxybutyl acrylate as a low Tg monomer, acrylic acid as a high Tg monomer, and hydroxyethyl acrylate as a mid Tg monomer.

10. The antimicrobial pressure sensitive adhesive precursor composition of claim 1, wherein the chelator is present in an amount of about 1 wt % to about 25 wt % with respect to the weight of the antimicrobial pressure sensitive adhesive precursor composition.

11. The antimicrobial pressure sensitive adhesive precursor composition of claim 1, wherein the chelator is selected from the group consisting of citric acid, tartaric acid, malic acid, ethylenediaminetetraacetic acid, salts thereof, and combinations thereof.

12. The antimicrobial pressure sensitive adhesive precursor composition of claim 1, wherein the water-soluble plasticizer is present in an amount of about 3 wt % to about 25 wt % with respect to the weight of the antimicrobial pressure sensitive adhesive precursor composition.

13. The antimicrobial pressure sensitive adhesive precursor composition of claim 1, wherein the water-soluble plasticizer is selected from the group consisting of glycerol, polyglycerol-3, polyglycerol-4, polyglycerol-6, polyglycerol-10, diethylene glycol, polyethylene glycol of an average weight from about 300 to about 800, and combinations thereof.

14. The antimicrobial pressure sensitive adhesive precursor composition of claim 1, further comprising water in an amount of less than about 0.1 wt %.

15. The antimicrobial pressure sensitive adhesive precursor composition of claim 1, wherein the polymerizable mixture is present.

16. The antimicrobial pressure sensitive adhesive precursor composition of claim 1, wherein the partially polymerized composition of the polymerizable mixture is present.

17. A method for preparing an antimicrobial pressure-sensitive adhesive, the method comprising:

providing the antimicrobial pressure sensitive adhesive precursor composition of claim 15, irradiating the antimicrobial pressure sensitive adhesive precursor composition with electromagnetic radiation at a wavelength of about 280 to 500 nanometers at an average light intensity of about 0.01 to about 20 milliwatts per centimeter squared (mW/cm$^2$), to partially polymerize the polymerizable mixture, and subsequently curing the antimicrobial pressure sensitive adhesive precursor composition by further irradiating the antimicrobial pressure sensitive adhesive precursor composition with electromagnetic radiation at a wavelength of about 280 to 500 nm wavelength at an average light intensity of greater than about 20 mW/cm$^2$ to form the antimicrobial pressure-sensitive adhesive.

18. A method for preparing an antimicrobial pressure-sensitive adhesive, the method comprising:

providing the antimicrobial pressure sensitive adhesive precursor composition of claim 16; and subsequently curing the antimicrobial pressure sensitive adhesive precursor composition by irradiating the antimicrobial pressure sensitive adhesive precursor composition with electromagnetic radiation at a wavelength of about 280 to 500 nm wavelength at an average light intensity of greater than about 20 $mW/cm^2$ to form the antimicrobial pressure-sensitive adhesive.

19. An antimicrobial pressure-sensitive adhesive prepared by the method of claim 17.

20. An antimicrobial pressure-sensitive adhesive prepared by the method of claim 18.

21. An antimicrobial article comprising:

a substrate comprising a first surface and a second surface opposite the first surface; and an antimicrobial pressure sensitive adhesive disposed on the first surface;

wherein the antimicrobial pressure sensitive adhesive is the antimicrobial pressure sensitive adhesive of claim 19 or the antimicrobial pressure sensitive adhesive of claim 20.

22. A method comprising:

providing the antimicrobial article of claim 21; and contacting the antimicrobial pressure sensitive adhesive of the antimicrobial article to a surface for a period of time, wherein the contacting results in one or more of:

reducing the number of microorganisms on the surface, preventing the formation or growth of a biofilm on the surface, and disrupting an existing biofilm on the surface.

23. A method for treating or preventing an infection, the method comprising:

providing the antimicrobial article of claim 21, and contacting the antimicrobial pressure sensitive adhesive of the antimicrobial article to a surface in need of disinfecting for a period of time, wherein the contacting is effective to reduce one or more symptoms of infection, and wherein the contacting is effective to prevent the onset of an infection characterized by the presence of one or more symptoms of infection.

24. A kit comprising:

the antimicrobial article of claim 21; and a set of instructions directing a user to contact the antimicrobial article to a surface.

* * * * *